United States Patent [19]

Nader et al.

[11] Patent Number: 5,082,965

[45] Date of Patent: Jan. 21, 1992

[54] PROCESS FOR PREPARATION OF ALKOXYCARBONYLOXYSTYRENE

[75] Inventors: Allan E. Nader; Thaliyil V. Rajanbabu, both of Wilmington, Del.

[73] Assignee: E. I. Du Pont de Nemours and Company, Wilmington, Del.

[21] Appl. No.: 604,985

[22] Filed: Oct. 29, 1990

[51] Int. Cl.⁵ ............................................. C07C 69/96
[52] U.S. Cl. ...................................................... 558/270
[58] Field of Search ........................................ 558/270

[56] References Cited

U.S. PATENT DOCUMENTS 4,491,628  1/1985  Ito et al. ............................. 430/176
4,503,271  3/1985  Fujiwara et al. .................... 568/799

FOREIGN PATENT DOCUMENTS 47129  4/1974  Australia .

OTHER PUBLICATIONS

Houlihan, et al., *Can Chem.*, vol. 63, pp. 153-162 (1985).
Corson, et al., *J. Org. Chem.*, vol. 23, pp. 544-549, (1958).
McKean et al., *J. Org. Chem.*, vol. 52, pp. 422-425 (1985).
Kauffmann et al., *Angew. Chem. Int. Ed. Engl.*, 25, (10), 909-911 (1986).
Yamashita et al., *Bull. Chem. Soc. Jpn.*, 57, 2335-2336 (1984).
Fréchet et al., *Polymer*, 24, 995-1000 (1983).

*Primary Examiner*—Paul J. Killos

[57] ABSTRACT

The present invention provides a process for the preparation of alkoxycarbonyloxystyrene comprising reacting acyloxystyrene with a strong base to yield a phenolate to which is added an alkoxycarbonylating agent in an organic solvent and a phase transfer catalyst to yield the desired product in the organic phase.

15 Claims, No Drawings

PROCESS FOR PREPARATION OF ALKOXYCARBONYLOXYSTYRENE

FIELD OF THE INVENTION

The present invention relates to a process for the preparation of alkoxycarbonyloxystyrenes from an acyloxystyrene by in situ hydrolysis followed by alkoxycarbonylation.

BACKGROUND OF THE INVENTION

Alkoxycarbonyloxystyrenes, especially 4-t-butoxycarbonyloxystyrene, are valuable monomers used in the manufacture of specialty polymers. Incorporation of the monomer into a polymer backbone by polymerization via the olefin group affords a polymer with a pendant reactive functional group, i.e., the pendant alkoxycarbonyloxy group. An especially important area of use for 4-t-butoxycarbonyloxystyrene is in the manufacture of poly(4-t-butoxycarbonyloxystyrene) which is used in the manufacture of photoresists. Known methods for preparing alkoxycarbonyloxystyrenes employ expensive Wittig reaction chemistry. The process of the present invention affords an economical, one-pot synthesis route to these commercially valuable monomers.

Houlihan et al., Can. J. Chem., Vol. 63, pp. 153-162, (1985) discloses the t-butoxycarbonylation of phenols, alcohols, enols, thiols and phenolic polymers such as poly(p-hydroxystyrene) by reaction with di-tertbutyl dicarbonate under phase transfer conditions. Typical phase transfer catalysts such as the crown ethers can be employed, but the uncatalyzed reaction is preferred in the presence of potassium carbonate as it gives the t-butoxycarbonyloxy substituted polymer in quantitative yield while greatly simplifying purification. There is no mention of the t-butoxycarbonylation of monomeric styrenes or using substituted styrene compounds, such as acetoxystyrene, as a precursor.

U.S. Pat. No. 4,461,628 of Ito et al., issued Jan. 1, 1985 teaches the preparation of t-butoxycarbonyloxystyrene by reaction of p-hydroxybenzaldehyde with di-t-butyldicarbonate in the presence of base to yield p-t-butoxycarbonyloxybenzaldehyde, which is then reacted with methyltriphenylphosphonium bromide and potassium t-butoxide to yield the desired product.

Corson et al., J. Org. Chem., Vol. 23, pp. 544-549 (1958) disclose the preparation of vinylphenols and isopropenylphenols. In particular, the hydrolysis of p-acetoxystyrene to p-hydroxystyrene is taught to be quantitative under conditions so gentle that no purification of the p-hydroxystyrene is required.

Alkoxy styrenes have also been prepared by many other processes known in the art. Examples include palladium catalyzed cross-coupling, various equivalents of Wittig chemistry, dehydration of methyl phenyl carbinols, dehydrogenation of p-ethyl phenol and malonic acid synthesis.

The known methods for the preparation of alkoxycarbonyloxystyrenes are complex multi-step processes that commonly employ expensive reagents. They do not afford convenient one-pot synthetic routes to the alkoxycarbonyloxystyrene monomers. Some of these methods require the preparation of 4-hydroxy styrene as an isolatable intermediate. These methods suffer from the fact that 4-hydroxystyrene is known to be unstable, subject to ready and uncontrollable polymerization, and toxic.

Alternate routes to the commercially valuable polymers containing pendant alkoxycarbonyloxy groups depend on introduction of the alkoxycarbonyloxy group after formation of the styrene polymer. This approach necessitates isolation and purification of a polymeric product from the alkoxycarbonylation reaction mixture. Use of the polymers made from the monomers of the present invention in photoresists require a high degree of purity. It is well known in the art that it is preferable to prepare high purity polymers from high purity monomers rather than carry out chemical reactions and purifications with polymeric species.

It is therefore an object of the present invention to provide a process for the preparation of alkoxycarbonyloxystyrene from a readily available styrene.

It is a further object of the present invention to provide a simple one-pot, two-phase reaction for the alkoxycarbonylation of a substituted styrene with no isolation of an hydroxystyrene intermediate.

It is a further object of the present invention to provide an economical route for the preparation of t-butoxycarbonyloxystyrene.

SUMMARY OF THE INVENTION

The present invention comprises a process for the preparation of alkoxycarbonyloxystyrene comprising:
a) reacting an acyloxystyrene with an aqueous strong base to yield the corresponding phenolate;
b) adding an alkoxycarbonylating agent in an organic solvent and a phase transfer catalyst to the above phenolate reaction to yield the desired alkoxycarbonyloxystyrene in the organic phase; and
c) isolation of the desired alkoxycarbonyloxystyrene.

DETAILED DESCRIPTION OF THE INVENTION

The present invention provides a process for the preparation of alkoxycarbonyloxystyrene from an acyloxystyrene by in situ hydrolysis followed by alkoxycarbonylation. The process of the present invention is summarized in reaction Scheme I.

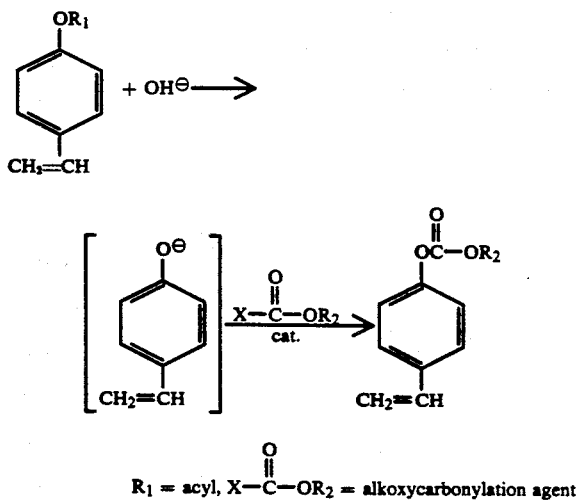

The initial step of the process of the present invention comprises reacting an acyloxystyrene with a strong base to yield the corresponding phenolate. Preferably distilled starting materials are employed. Acyloxystyrenes suitable for use in this reaction include those having from 1 to 4 carbon atoms in the acyl group. Other substituents which do not interfere with the process of this invention can be present on the styrene ring. Preferred for use herein is 4-acetoxystyrene.

Suitable bases for use in the present invention include aqueous alkali metal hydroxides, or carbonates. Preferred bases are the alkali metal hydroxides such as potassium hydroxide or sodium hydroxide. Use of carbonates results in a slow reaction with low yields. The base is first dissolved in water and the acyloxystyrene is then added with stirring.

This reaction is conducted at a temperature of from about 0° C to about 60° C. Preferably it is conducted at a temperature range of from about 20° C. to about 25° C. at ambient atmospheric pressure. Oxygen and carbon dioxide are desirably excluded from this reaction. Therefore, the reaction is carried out under an inert atmosphere, preferably nitrogen or argon. Vigorous agitation is recommended.

Isolation of the resulting phenolate is not required. A phase transfer catalyst and an alkoxycarbonylation agent in an organic solvent are added to the reaction mixture. Slow addition of the alkoxycarbonylation agent is recommended with close monitoring of the temperature to prevent overheating of the reaction mixture.

Suitable alkoxycarbonylation agents include alkyl substituted carbonates, formate, or haloformate compounds. Examples include, but are not limited to, di-t-butyldicarbonate, azido-t-buytlformate, t-butylchloroformate, t-butylfluoroformate, and like compounds. Preferred for use herein is di-t-butyldicarbonate. The mole ratio of alkoxycarbonylation agent to acyloxystyrene is from about 3:1 to about 1:1. The mole ratio preferably employed is about 1:1.

Solvents suitable for use in this reaction include organic solvents such as tetrahydrofuran, methylenechloride, 1,2-dichloroethane, or glyme. The preferred solvent is tetrahydrofuran.

Phase transfer catalysts appropriate for use herein include alkyl or aryl ammonium or phosphonium salts such as the chloride, bromide, iodide, or hydrogensulfate salts. Also suitable are the crown ethers such as 18-crown-6. Alkyl ammonium salts are preferred, in particular, tetrabutylammonium hydrogen sulfate.

The reaction of the phenolate formed in situ with the alkoxycarbonylation agent is conducted at a temperature of from about -10° C. to about 30° C., preferably at about 0° C. to about 20° C. The reaction is carried out at ambient atmospheric pressure under an inert atmosphere such as nitrogen or argon. Vigorous agitation is required.

The progress of the reaction can easily be followed by silica gel thin layer chromatography or other equivalent techniques. When all of the starting material has been consumed, additional organic solvent is added to the reaction mixture to aid in easy separation of the organic phase. After separation of the organic and aqueous phases, the desired alkoxycarbonyloxystyrene product is isolated using conventional known techniques, such as distillation. Overall reaction time is from about 1 to about 3 hours.

The process of this invention facilitates reaction in the organic phase via the phase transfer reaction. The desired alkoxycarbonyloxystyrene product in the organic phase is protected from reaction with the base in the aqueous phase, and is easily isolated by separation of the organic and aqueous phases. If desired, the product can be derivatized directly in the organic phase after separation without isolation or purification.

The process of the present invention is especially useful for the economical preparation of the monomer 4-(t-butoxycarbonyloxy)styrene, which when polymerized is widely used in the photoresist industry.

The following examples illustrates the process of the present invention, but are not intended to limit it in any way.

EXAMPLE 1

Potassium hydroxide (115.0 g, 2.05 m) was dissolved in 1490 mL of water in a mechanically-stirred flask under nitrogen. To the solution at room temperature was added 151.0 g (0.932 m) of 4-acetoxystyrene, and the mixture was stirred until it was homogenous (ca. 1 hr). To the solution was added 9.32 g (0.027 m) of tetrabutylammonium hydrogen sulfate followed by 203.4 g (0.93 m) of di-t-butyldicarbonate in 290 mL of tetrahydrofuran. The addition of the carbonate was done over 30 minutes and the temperature was carefully monitored to maintain it around 15° C. The reaction was followed by silica gel thin layer chromatography (20% ether in hexane). When all the starting material was consumed, IL of ether was added to the reaction mixture and the organic layer was separated. The aqueous layer was further extracted with more ether (3×500 mL) and the combined ether extracts were subsequently washed with cold 10% sodium hydroxide, ammonium chloride and brine. The product, 4-(t-butoxycarbonyloxy)styrene (190.4 g, 93%) was purified by distillation under vacuum, b.p. 80°-95° C./0.05 mmHg. The purity of the various fractions were ascertained by high performance liquid chromatography (silica, ether/hexane), capillary gas chromatography (2% HP methyl silicone, 25M, 0.2 ID column programmed to run at 60° C. for 5 min., increasing to 250° C. at a rate of 20 degrees per min.), and nuclear magnetic resonance spectroscopy.

EXAMPLE 2

In a mechanically stirred flask under nitrogen was dissolved 6.17 g (0.11 m) of potassium hydroxide in 77 mL of water. To the solution was added, with good stirring, 8.10 g (0.05 m) of 4-acetoxystyrene. The mixture was stirred for 1 hour at which time it turned homogeneous. To the solution was added 0.50 g (.0015 m) of the phase transfer catalyst. The reaction was cooled down to 0° C. and a solution of 14.0 g (0.064 m) of di-t-butyldicarbonate was added drop wise over 15 min. The cold bath was removed and the mixture was warmed to room temperature. Additional 100 mL of methylene chloride was then added and the reaction was continued for 4 more hours. Excess methylene chloride was then added and the organic layer was separated and was successively washed with 2% sodium hydroxide, ammonium chloride and brine. It was then dried using anhydrous MgSO4 and the product, 4-(t-butoxycarbonyloxy)styrene (5.7 g, 51.8%) was distilled under vacuum.

EXAMPLE 3

In 100 mL of methylene chloride was dissolved 6.91 g (0.043 m) of 4-acetoxystyrene, 13.10 g (0.060 m) of di-t-butyldicarbonate and 0.50 g (0.0014 m) of tetrabutyl ammonium hydrogensulfate under nitrogen. The mixture was cooled at 0° C. and a solution of 4.40 g (0.110 m) of sodium hydroxide solution was added in 30 minutes with good stirring. It was subsequently warmed to room temperature. The reaction was followed by thin layer chromatography on silica gel using 10% ether/hexane as the solvent. After 7 hours at room temperature 200 mL of methylene chloride was added and the organic layer was separated. It was washed with 100 mL of ammonium chloride, and 100×2 mL of saturated sodium chloride. The organic layer was then dried and concentrated and the product, 4-(t-butoxycarbonyloxy)styrene, was analyzed by NMR, HPLC and TLC. The yield was approximately 40%.

EXAMPLE 4

In 200 mL of methylene chloride was dissolved 6.91 g (0.043 m) of 4-acetoxystyrene and 13.10 g (0.060 m) of di-t-butyldicarbonate under nitrogen. To the solution at room temperature was added 14.0 g (0.101 m) of potassium carbonate and the mixture was vigorously stirred for 22 hours, following the reaction by thin layer chromatography. After 22 hours at room temperature 100 mL of THF was added and the reaction was further stirred for 142 hours. It was worked up as in the above Examples. There was a very low yield (less than 10 %) of the product, 4-(t-butoxycarbonyloxy)styrene, under these conditions as analyzed by NMR, HPLC and TLC.

What is claimed is:

1. A process for the preparation of alkoxycarbonyloxystyrene comprising:
    a) reacting acyloxystyrene with a strong base to yield the corresponding phenolate;
    b) adding to said phenolate reaction a phase transfer catalyst and an alkoxycarbonylation agent in an organic solvent to yield alkoxycarbonyloxystyrene in the organic phase; and
    c) separating the organic phase and isolating the desired alkoxycarbonyloxystyrene.

2. The process of claim 1 wherein the acyloxystyrene has from 1 to 4 carbon atoms in the acyl group.

3. The process of claim 2 wherein the acyloxystyrene is 4-acetoxystyrene.

4. The process of claim 1 wherein the base comprises potassium hydroxide or sodium hydroxide.

5. The process of claim 1 wherein the phase transfer catalyst comprises an alkyl or aryl ammonium halide or hydrogen sulfate salt, an alkyl or aryl phosphonium halide or hydrogen sulfate salt, or a crown ether.

6. The process of claim 5 wherein the phase transfer catalyst is tetrabutylammonium hydrogen sulfate.

7. The process of claim 1 wherein the alkoxycarbonylation agent comprises an alkyl substituted carbonate, formate or haloformate.

8. The process of claim 7 wherein the alkoxycarbonylation agent is di-t-butyldicarbonate.

9. The process of claim 1 wherein the solvent is selected from tetrahydrofuran, methylenechloride, 1,2-dichloroethane, or glyme.

10. The process of claim 9 wherein the solvent is tetrahydrofuran.

11. The process of claim 1 wherein the mole ratio of acyloxystyrene to alkoxycarbonylation agent is from about 1:3 to about 1:1.

12. The process of claim 1 in which step a) is conducted at a temperature of from about 0° C. to about 60° C.

13. The process of claim 1 in which step b) is conducted at a temperature of from about -10° C. to about 30° C.

14. The process of claim 1 conducted under an inert atmosphere.

15. The process of claim 1 wherein the alkoxycarbonyloxystyrene prepared is 4-t-butoxycarbonyloxystyrene.

* * * * *